(12) United States Patent
Tjioe et al.

(10) Patent No.: US 7,045,623 B2
(45) Date of Patent: May 16, 2006

(54) METHOD FOR CONTACTING MOLTEN UREA WITH A GAS STREAM

(75) Inventors: Tjay Tjien Tjioe, Sittard (NL); Henricus Antonius Maria Duisters, Budel (NL)

(73) Assignee: DSM IP Assets B.V., Heerlen (NL)

( * ) Notice: Subject to any disclaimer, the term of this patent is extended or adjusted under 35 U.S.C. 154(b) by 43 days.

(21) Appl. No.: 10/478,517

(22) PCT Filed: Jun. 6, 2002

(86) PCT No.: PCT/NL02/00368

§ 371 (c)(1),
(2), (4) Date: Nov. 24, 2003

(87) PCT Pub. No.: WO02/100840

PCT Pub. Date: Dec. 19, 2002

(65) Prior Publication Data

US 2004/0171831 A1    Sep. 2, 2004

(30) Foreign Application Priority Data

Jun. 13, 2001 (NL) .................................... 1018283

(51) Int. Cl.
*C07D 251/60*     (2006.01)
(52) U.S. Cl. ......................................... 544/201; 564/73
(58) Field of Classification Search ................ 544/201; 564/73
See application file for complete search history.

(56) References Cited

U.S. PATENT DOCUMENTS

| 4,565,867 A | 1/1986 | Best et al. ................... 544/201 |
| 5,384,404 A | 1/1995 | Lee ............................. 544/201 |

FOREIGN PATENT DOCUMENTS

EP     808 836     11/1997

*Primary Examiner*—Peter O'Sullivan
(74) *Attorney, Agent, or Firm*—Mayer, Brown, Rowe & Maw LLP

(57) ABSTRACT

The invention relates to a method for contacting molten urea with a gas stream that contains ammonia and/or carbon dioxide, in which use is made of an additional stream the temperature of which differs from the temperature of the molten urea and/or the gas stream. The additional stream preferably contains ammonia. The method is preferably part of a process for the preparation of melamine.

15 Claims, No Drawings

METHOD FOR CONTACTING MOLTEN UREA WITH A GAS STREAM

CROSS REFERENCE TO FELATED APPLICATION

This application is a 371 of PCT/NL02/00368, filed Jun. 2002 which designated the U.S., and that International Application was published under PCT Article 21(2) in English.

METHOD FOR CONTACTING MOLTEN UREA WITH A GAS STREAM

The invention relates to a method for contacting molten urea with a gas stream containing ammonia and/or carbon dioxide.

Such a method is applied on an industrial scale in for instance processes for the preparation of melamine, for instance as part of a high-pressure process for the preparation of melamine, which is disclosed in U.S. application Ser. No. 4,565,867. In the process according to U.S. application Ser. No. 4,565,867 molten urea is supplied to a scrubber unit. In the scrubber unit the molten urea, with a temperature of for instance 280° F. (138° C.) and a pressure between 1700 psi and 2200 psi (between 11.7 MPa and 15.2 MPa), is contacted with a gas stream consisting mainly of ammonia and carbon dioxide and also containing melamine vapour and having a temperature between 670° F. and 800° F. (between 354° C. and 427° C.). This gas stream comes from a gas/liquid separator placed downstream of the melamine reactor in which the composition from the reactor is separated into a melamine melt and the gas stream. The urea scrubs the melamine vapour from the gas stream, and is also heated by the gas stream. The urea, which has been heated to between 350° F. and 450° F. (between 177° C. and 232° C.) and which has absorbed the melamine vapour, is subsequently sent to the melamine reactor to be converted into melamine. The gas stream, which has been cooled to between 177° C. and 232° C. and which contains virtually no melamine, is processed further, for instance by recycling it to a urea plant.

Because of the high temperature of the gas stream leaving the gas/liquid separator there is a risk of the molten urea being excessively heated, so that undesirable chemical reactions will take place, such as the formation of biuret, which may, among other things, lead to deposition of solids in the scrubber unit, so that the unit is clogged. If the temperature becomes too high, the contents of the scrubber unit are to be cooled, via a cooled wall and/or by means of cooling pipes in the scrubber unit. The heat thus recovered from the scrubber unit will be available for, for instance, steam generation. In addition, the same scrubber unit is also used as a heating unit, for instance during non-stationary situations such as start-up, maintenance shutdowns or temporary reactor failures.

The disadvantage of the known method is that the scrubber unit, this being the apparatus in which the method for contacting the molten urea with the gas stream is carried out, must be of a complex design owing to the presence of cooling/heating device needed to supply the required cooling capacity or to be able to raise the temperature of the molten urea to the desired level or maintain it at this level. These requirements lead to high investment costs.

The aim of the invention is to largely avoid said disadvantages. This aim is achieved according to the invention in that use is made of an additional stream the temperature of which differs from the temperature of the molten urea and/or the gas stream.

The advantage of the method according to the invention is that the cooling/heating device belonging to the apparatus in which the molten urea is contacted with the gas stream can have lower cooling and heating capacities than in the known method and can thus be cheaper.

The molten urea feed consists, as is known for processes for the preparation of urea or for the preparation of melamine from urea, mainly of urea, but may in addition contain ammonia and/or carbon dioxide up to an amount that has the saturation vapour pressure at the prevailing scrubber unit temperature. In addition, the molten urea may contain water: less than 3 wt. %, usually less than 0.5 wt. %. The temperature of the molten urea may vary within wide limits and will generally lie between the melting point at the prevailing pressure and the temperature at which significant decomposition reactions occur. The temperature of the molten urea will usually lie between 130° C. and 260° C. The pressure of the molten urea may vary within wide limits and will generally be determined partly by the pressure of the gas stream and the pressure at which further processing of the urea takes place. The pressure of the molten urea will usually lie between 0.1 MPa and 30 MPa.

The molten urea feed is contacted with the gas stream, which will be discussed in more detail below. The contacting can be done in the ways known to one skilled in the art. Contacting can for instance take place in a bubble column: a column that is filled mainly with molten urea through which the gas stream is passed. Contacting can also take place in, for instance, a gas-filled, packed column, in which the gas phase is the continuous phase and the liquid flows down along the packing as a film, resulting in close contact between the liquid and the gas phase.

The gas stream that is contacted with the molten urea in the method according to the invention contains ammonia and/or carbon dioxide. Depending on the way in which the gas stream has been formed, such as for instance in a process for the preparation of melamine, in which the gas stream will usually contain ammonia and carbon dioxide, the gas stream may additionally contain other substances, such as for instance water or melamine, which as a rule do not substantially affect the operation of the method according to the invention. The temperature of the gas stream may vary within wide limits. It is advantageous for the temperature to be 130° C. or higher, so that solidification of the urea is prevented. It is also advantageous for the temperature of the gas stream to be lower than 480° C., preferably lower than 430° C., to prevent decomposition of the molten urea. The pressure of the gas stream may vary within wide limits and will partly be determined by the pressure at which the gas stream was formed, such as for instance the pressure in a process for the preparation of melamine, and by the pressure at which further processing of the gas stream takes place. The pressure of the gas stream will usually lie between 0.1 MPa and 30 MPa. If the gas stream contains ammonia and carbon dioxide, the ammonia:carbon dioxide weight ratio is preferably 3:1 or higher, more preferably 5:1 or higher: The advantage of a high proportion of ammonia in the gas stream is that decomposition reactions of the molten urea are suppressed. The gas stream as a whole preferably contains at least 40 wt. % ammonia.

An additional stream is here understood to mean a substance or a mixture of substances, in the liquid phase and/or in the gas phase, which is not the molten urea or the gas stream. It is advantageous if the additional stream has the same pressure, or is given the same pressure, as the molten urea, the gas stream, or the apparatus in which the contacting takes place, or a somewhat higher pressure, so that it will be easier to use the additional stream. This may mean, here and hereinafter, that the additional stream is no longer gaseous and/or liquid, but reaches or is in supercritical condition. The additional stream has a different temperature. This is understood to mean that the temperature of the additional stream differs by at least 5° C. from at least one of the following temperatures: the temperature of the molten urea or the temperature of the gas stream. The different temperature of the additional stream makes it possible to achieve a temperature control effect. The degree of temperature control depends on the temperature of the additional stream and its flow rate. Temperature and flow rate will therefore have to be set so that the intended temperature change takes place. This can be done on the basis of heat content calculations, optionally supplemented with experiments. The wording "use is made of an additional stream" is understood to mean that the additional stream is supplied to the molten urea or to the gas stream, prior to contacting, or directly to the apparatus where contacting takes place. This brings the additional stream into direct contact with the molten urea and/or the gas stream.

The scrubber unit, defined as an apparatus in which the method according to the invention is carried out, may be a separate unit, as described in the aforementioned known method; the scrubber unit may, however, also be part of a bigger unit, such as a unit in a process for the preparation of melamine in which both the method according to the invention is carried out and the reaction of urea to form melamine. The scrubber unit may be designed in many different ways, for instance as a bubble column or a packed column. The molten urea, the gas stream and the additional stream can be cocurrent or countercurrent with each other.

The additional stream may contain a large number of substances or combinations thereof. One criterion for determining the composition is the intended further use of the gas stream and/or the molten urea, the additional stream being combined with the outflowing gas stream and/or the molten urea. Examples of substances which the additional stream may contain are: nitrogen, urea, ammonia, carbon dioxide, water and ammonium carbamate. The additional stream preferably contains ammonia or carbon dioxide, or a mixture thereof; this has the advantage that the further processing of the molten urea or of the gas stream is not adversely affected by the presence of substances that would otherwise not be present. As indicated earlier, a high weight ratio between ammonia and carbon dioxide, preferably 3:1 or higher, during the contacting of the gas stream with molten urea is preferred. It may be advantageous, therefore, if the additional stream is essentially free of carbon dioxide. More preferably, the additional stream contains mainly ammonia.

The additional stream is preferably liquid. This has the advantage that, in comparison with an additional stream that contains a gas phase, the volume to be treated is smaller and that any pressure adjustments can be realized in a technically simpler and therefore cheaper manner. Preferably, said additional liquid stream contains mainly liquid ammonia. This has the advantage that, if the method according to the invention forms part of a melamine preparation, the formation of undesirable oxygen-containing by-products can be reduced.

In a further preferred embodiment the temperature of the molten urea and/or the gas stream and/or the scrubber unit during contacting is set entirely by means of the additional stream, so that there is no need at all for the cooling/heating device. This has the advantage that the design of a scrubber unit can technically be greatly simplified and thus becomes cheaper. A further advantage of this further preferred embodiment according to the invention is that there is no need for any cooling or heating surface areas that are susceptible to scaling, so that maintenance of the scrubber unit will become technically simpler and thus cheaper. In addition, it is also possible for existing scrubber units that are already provided with a heating/cooling device to benefit from this further preferred embodiment since a saving is achieved on the running costs of the indirect temperature control, such as energy supply or maintenance.

There are various ways in which the additional stream can be used in the method according to the invention. The additional stream can for instance be combined with the molten urea or with the gas stream. This yields a combined stream. The combined stream is subsequently fed to the scrubber unit so that the combined stream is contacted with the gas stream (if the combined stream contains the molten urea), or with the molten urea (if the combined stream contains the gas stream). This has the advantage that no additional inlet in the scrubber unit is needed to apply the method according to the invention. This is advantageous in particular when existing processes are optimized. In this embodiment it is important to ensure, for instance by setting the amounts and/or the temperature of the additional stream, that good process operation is not endangered. Good process operation may be endangered when, for instance, a large amount of solid material is formed in the molten urea or in the gas stream.

Formation of a large amount of solid material in the molten urea or in the gas stream may take place as a result of a temperature rise or drop caused by the introduction of the additional stream. This may result in clogged lines. Examples of solid formation resulting from temperature changes are: solidification of urea; formation of biuret from urea at temperatures above 260° C.; formation of solid melamine particles in the gas stream. The amount of solid in the molten urea is preferably less than 20 wt. %, more preferably less than 10 wt. %. The amount of solid in the gas stream is preferably less than 3 wt. %, more preferably less than 0.3 wt. %. Said weight percentages are valid before, during and after application of the method according to the invention. If formation of solids takes place outside said preferred limits, it may be necessary to adjust the amount of the additional stream. It may therefore be advantageous not to use the additional stream via combination with the existing streams that are fed to the scrubber unit, but to use it as a separate stream, in the scrubber unit itself, allowing a wider temperature control range. Preferably the additional stream is to be fed to the scrubber unit at a location where good mixing with the contents of the scrubber unit is possible; this is advantageous for achieving good temperature control. Good mixing takes place, for instance, if the additional stream is introduced at a location where there is already a flow present in the scrubber unit, also in the absence of the additional stream. Preferably the additional stream comes into contact with flowing material in the scrubber unit, which contains both the molten urea and the gas stream.

The method according to the invention is preferably carried out as part of a continuous process for the preparation of melamine from urea at a pressure between 0.1 and 30 MPa. In such a process the molten urea feed and the gas stream released upon the conversion of urea into melamine can as a rule directly be applied in the method according to the invention. Besides ammonia and/or carbon dioxide the gas stream may then also contain melamine; the melamine is absorbed by the molten urea during contacting so as to be returned to the reactor. Another advantage of the use of the method according to the invention in a continuous process for the production of melamine from urea is that the method allows the use of various streams of differing temperatures that are already present and that can, without substantial adaptation, be used as additional stream in the method according to the invention. This can for instance be ammonia gas from the cooling step, where it can be used as a cooling medium for obtaining melamine powder. The method according to the invention is preferably used in a high-pressure, non-catalytic process for the preparation of melamine, during stationary operation and/or during start-up or shutdown procedures. Such processes are generally carried out at a pressure between 5 MPa and 30 MPa.

In another embodiment of the method according to the invention use is made of at least one further additional stream the temperature of which differs from the temperature of the molten urea and/or the gas stream. If use is made of several additional streams, each additional stream may have its own composition, as described above. The additional streams can be used in each of the ways described above. The advantage of this embodiment is that it allows more flexible use of available streams for optimum utilization of the available cooling or heating sources.

The industrial applicability of the method according to the invention is not restricted to high-pressure, non-catalytic processes for the preparation of melamine. The method according to the invention can also be applied in, for instance, low-pressure, catalytic processes for the preparation of melamine such as the BASF process as described in Ullmann's Encyclopaedia of Industrial Chemistry, Vol A16, Fifth Edition, pp. 174–175, or in Nitrogen 228 (July-August 1997), p. 46. The BASF process is carried out at a pressure of about 0.1–0.2 MPa. A gas stream that contains ammonia, carbon dioxide and optionally traces of melamine and that has a temperature of about 200° C. is fed to a scrubber unit where it is contacted with molten urea of about 135° C. The molten urea cools the gas stream and scrubs out any melamine that is present. The scrubber unit is provided with a heat exchanger, which discharges surplus heat in the form of steam. In such a process, application of the method according to the invention may allow the use of a smaller heat exchanger or even do away with the need for a heat exchanger: surplus heat will then be absorbed by the additional stream so that it will be available for use elsewhere.

The molten urea is, as indicated earlier, preferably used in a process for the preparation of melamine. In view of the fact that the gas stream, with which the molten urea has been brought into contact with, often contains carbon dioxide, the molten urea will then thereafter contain some dissolved carbon dioxide. The presence of carbon dioxide in molten urea, however, is a disadvantage in a process for the preparation of melamine because it can lead to corrosion. A further disadvantage of the presence of carbon dioxide in molten urea is that it will first be heated in the melamine reactor, only to be cooled again in the scrubber to which it will be returned, thus creating a carbon-dioxide loop which negatively influences the energy balance of the process without contributing to the result of the process.

It is therefore a further objective of the present invention to provide a method for the treatment of molten urea containing carbon dioxide whereby the amount of carbon dioxide is reduced.

Said further objective is achieved in that the method comprises the steps of:

bringing the molten urea into contact with an ammonia-containing stream, whereby gaseous carbon dioxide-enriched ammonia and molten urea having a reduced amount of carbon dioxide are formed;

separating the gaseous carbon dioxide-enriched ammonia from the molten urea having a reduced amount of carbon dioxide.

An advantage of this method according to the present invention is that corrosion is reduced, in piping through which the molten urea flows. A further advantage of this method according to the invention in a process for the preparation of melamine is that the carbon dioxide is not transported to and heated in the melamine reactor, thereby avoiding the earlier-mentioned carbon dioxide loop, thus positively influencing the energy balance of the whole melamine-preparing process.

The ammonia-containing stream preferably contains more than 90 mole % ammonia and more preferably consists essentially of gaseous ammonia. As a result of the contacting between the carbon dioxide containing molten urea and the ammonia-containing stream, the ammonia-containing stream is carbon-dioxide enriched; subsequently, it is separated and removed from the molten urea having a reduced amount of carbon dioxide.

Preferably, the molten urea having a reduced amount of carbon dioxide is used in a process for the preparation of melamine and the reduction of the carbon dioxide concentration in the molten urea is preferably more than 25% of the initial carbon dioxide concentration. The initial amount of carbon dioxide in the molten urea is usually higher than 0.5 wt %. The weight ratio gaseous ammonia:molten urea is preferably more than 0.05.

The contacting of the gaseous ammonia-containing stream and the carbon dioxide containing molten urea can be done in any gas-liquid contacting equipment e.g. a bubble column with or without internals like packing or sieve trays, a mostly gas containing strip column with packing or sieve trays, falling film equipment containing a multiple of pipes, a multiple of mostly liquid filled pipes with or without a draught tube.

In another preferred embodiment, the gaseous carbon dioxide-enriched ammonia is used as additional stream or as further additional stream during the contacting of the molten urea with the gas stream thereby enabling a combined, thus efficient, further processing of the various gaseous streams.

The invention will be elucidated by means of several examples and comparative experiments.

EXAMPLES I AND II AND COMPARATIVE EXPERIMENTS A AND B

In Examples I and II and in Comparative Experiments A and B, as shown in the table below, a stream of 6000 kg/hour of molten urea with a temperature of 138° C. is contacted with a gas stream in a scrubber unit. The cooling area is the heat exchanging area of the cooling/heating device in the scrubber unit that is needed to be able to control the temperature in the process at the given operating pressure, so that no problems such as solid formation occur and/or so that surplus heat is discharged from the scrubber unit.

TABLE

| No. | Gas stream | | | | Additional stream | | | Cooling |
| | Pressure (mPa) | Temp (° C.) | Flow rate (kg/h) | Composition* (wt. %) | Temp (° C.) | Flow rate (kg/h) | Component | area (m²) |
| --- | --- | --- | --- | --- | --- | --- | --- | --- |
| I | 0.2 | 250 | 6000 | 75/25/0 | 40 | 2000 | $NH_3$ (g) | none |
| A | 0.2 | 250 | 6000 | 75/25/0 | no additional stream | | | 50 |
| II | 20.5 | 405 | 4200 | 43/52/5 | 40 | 1800 | $NH_3$ (l) | none |
| B | 20.5 | 405 | 4200 | 43/52/5 | no additional stream | | | 200 |

Key to table
*Gas stream composition in wt. % of, respectively, $NH_3$, $CO_2$, melamine
(g) = gaseous
(l) = liquid As is clear from the above results, the additional stream can fully replace a cooling/heating device, both under conditions that are typical of a low-pressure, catalytic process for the preparation of melamine (Example I, Comparative Experiment A) and under conditions that are typical of a high-pressure, non-catalytic process for the preparation of melamine (Example II, Comparative Experiment B).

EXAMPLE III

A molten urea stream containing 5.4 w % of $CO_2$ at a pressure of 200 bar and a temperature 210° C. is treated with ammonia gas of 220° C. in a bubble column. The ammonia gas enters the column at the bottom and the $CO_2$ rich gas leaves the column at the top. The molten urea stream is 4 kg/h and the ammonia gas stream is 2.3 kg/h. The $CO_2$ content of the molten urea stream has been reduced to less than 0.5 w % after separation from the gas stream.

The invention claimed is:

1. Method for contacting molten urea with a gas stream that contains ammonia and/or carbon dioxide, wherein use is made of an additional stream comprising one or more of nitrogen, urea, ammonia, carbon dioxide, water or ammonium carbamate the temperature of which differs from the temperature of the molten urea and/or the gas stream, whereby the additional stream comes into direct contact with the molten urea and/or the gas stream.

2. Method according to claim 1, in which the gas stream contains ammonia and carbon dioxide.

3. Method according to claim 1, in which the additional stream contains ammonia, carbon dioxide or a mixture thereof.

4. Method according to claim 3, in which the additional stream contains liquid ammonia.

5. Method according to claim 1, in which the temperature during contacting is set by means of the additional stream.

6. Method according to claim 1, in which the additional stream is combined with the molten urea or with the gas stream, so that a combined stream is formed, after which the combined stream is contacted with the gas stream or with the molten urea, respectively.

7. Method according to claim 1, in which the additional stream is used as a separate stream.

8. Method according to claim 1, in which the gas stream also contains melamine.

9. Method according to claim 1, in which the method is part of a high-pressure, non-catalytic processes for the preparation of melamine.

10. Method according to claim 9, in which the method is applied during a start-up or shutdown procedure.

11. Method according to claim 1, in which use is made of at least one further additional stream the temperature of which differs from the temperature of the molten urea and/or the gas stream.

12. Method according to claim 1, further comprising the steps of:
   bringing the molten urea into contact with an ammonia-containing stream, whereby gaseous carbon dioxide-enriched ammonia and molten urea having a reduced amount of carbon dioxide are formed;
   separating the gaseous carbon dioxide-enriched ammonia from the molten urea having a reduced amount of carbon dioxide.

13. Method according to claim 12, wherein the gaseous carbon dioxide-enriched ammonia is used as additional stream or as further aditional stream according to claim 1.

14. Method for the treatment of molten urea containing carbon dioxide and having a temperature lying between 130° C. and 260° C., wherein the method comprises the steps of
   bringing the molten urea into contact with an ammonia-containing stream, whereby gaseous carbon dioxide-enriched ammonia and molten urea having a reduced amount of carbon dioxide are formed;
   separating the gaseous carbon dioxide-enriched ammonia from the molten urea having a reduced amount of carbon dioxide.

15. Method according to claim 14, wherein the molten urea having a reduced amount of carbon dioxide is used for the preparation of melamine.

* * * * *